US00PP21210P2

(12) United States Plant Patent
Van Den Top

(10) Patent No.: US PP21,210 P2
(45) Date of Patent: Aug. 17, 2010

(54) ***HOSTA* PLANT NAMED 'LITTLE TREASURE'**

(50) Latin Name: ***Hosta* hybrid (Tratt.)**
Varietal Denomination: Little Treasure

(76) Inventor: Hendrik Jan Van Den Top, Wesselseweg 46, 3771 PC Barneveld (NL)

( * ) Notice: Subject to any disclaimer, the term of this patent is extended or adjusted under 35 U.S.C. 154(b) by 102 days.

(21) Appl. No.: 12/287,538

(22) Filed: Oct. 10, 2008

(51) Int. Cl.
*A01H 5/00* (2006.01)

(52) U.S. Cl. ..... Plt./353

(58) Field of Classification Search ..... Plt./353
See application file for complete search history.

(56) References Cited

U.S. PATENT DOCUMENTS

PP12,663 P2 * 5/2002 Heemskerk ..... Plt./353
PP19,539 P3 * 12/2008 van den Top ..... Plt./353

OTHER PUBLICATIONS

UPOV ROM GTITM Computer Database, GTI Jouve Retrieval Software 2009/05 Citation for 'Little Treasure'.*

* cited by examiner

*Primary Examiner*—Wendy C. Haas
(74) *Attorney, Agent, or Firm*—Audrey Charles

(57) ABSTRACT

A new and distinct cultivar of *Hosta* plant named 'Little Treasure', characterized by its broadly spreading foliage with upright flower scapes, widely-margined green and light yellow variegated foliage, violet-colored flowers that are positioned above the foliage on strong scapes, and good garden performance.

2 Drawing Sheets

Latin name of genus an species of plant claimed: *Hosta* hybrid (Tratt.).

Variety denomination: 'Little Treasure'.

BACKGROUND OF THE INVENTION

The present invention relates to a new and distinct cultivar of *Hosta* plant botanically known as *Hosta* hybrid and hereinafter referred to by the cultivar name 'Little Treasure'.

The new *Hosta* cultivar is a naturally-occurring sport of 'Little Jay', U.S. Plant Pat. No. 11/704,810, characterized by lance-shaped, dwarf-sized, leaves with blue green margins, light yellow to creamy leaf centers, vertical flower scapes with light purple flowers, suitable for landscape, potted culture, or cut flower arrangements. The new cultivar was discovered as a whole plant and selected during August 2005 in a controlled environment at Barneveld, The Netherlands.

Asexual reproduction of the new Hosta by division and tissue culture in a controlled environment in Barneveld, The Netherlands since 2005, has shown that the unique features of this new Hosta are stable and reproduced true to type in successive generations.

SUMMARY OF THE INVENTION

The following characteristics of the new cultivar have been repeatedly observed and can be used to distinguish 'Little Treasure' as a new and distinct cultivar of Hosta plant:

1. Broadly spreading foliage with upright flower scapes;
2. Widely-margined green and light yellow variegated foliage;
3. Violet-colored flowers that are positioned above the foliage on strong scapes; and
4. Good garden performance.

Of the many commercially available *Hosta* cultivars, the most similar in comparison to the new cultivar is the parent cultivar 'Little Jay', U.S. Plant Pat. No. 19,539. However, in side by side comparisons, plants of the new cultivar differ from its parent, in leaf color and width of the leaf margin.

BRIEF DESCRIPTION OF THE DRAWINGS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Little Treasure'. The plants were grown outdoors in 3-liter containers for approximately two years in Barneveld, The Netherlands.

The photograph on the first sheet is a side perspective view of typical plants of 'Little Treasure' grown in an outdoor nursery.

The photograph at the top of the second sheet is a close-up view of a typical leaf of 'Little Treasure'.

The photograph at the bottom of the second sheet is a close-up view of a typical inflorescence of 'Little Treasure'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in June 2008 under natural light conditions in Barneveld, The Netherlands when day temperatures ranged from 12° C. to 31° C. (53° ° F. to 88° F.) and night temperatures ranged from 4° C. to 16° C. (39° F. to 61° F.).

Plants used in the following description were grown in Barneveld, The Netherlands, in an outdoor nursery in 3-liter containers and under conditions which closely approximate commercial production conditions. The plants were grown for approximately two years when the description was taken. Measurements and numerical values represent averages of typical plants.

Botanical classification: *Hosta* hybrid cultivar Little Treasure.

Parentage: Naturally-occurring sport of *Hosta* hybrid 'Little Jay', U.S. Plant Pat. No. 19,539.

Propagation:

*Type.*—*In vitro* propagation utilizing typical methods for *Hosta* is preferred, garden division is also possible.

*Time to initiate roots.*—Approximately 20 days at a temperature of approximately 15° C.

*Time to produce a rooted plant.*—Approximately 50 days at a temperature of approximately 15° C.

*Root description.*—Medium thickness, fibrous; creamy white in color.

*Rooting habit.*—Moderately branching, moderate density.

Plant description:

*Growth habit and general appearance.*—Herbaceous flowering perennial plant. Broadly spreading foliage with upright flower scapes. Flowering stems and leaves basal rosettes; moderately vigorous growth habit. Violet-colored flowers are positioned above the foliage on strong scapes.

*Crop time.*—Approximately 20 weeks from tissue culture plantlets to finish in an 11 cm container.

*Size.*—Plant height (soil level to top of foliar plane): Approximately 18.1 cm. Plant height (soil level to top of inflorescences): Approximately 44.8 cm. Plant width (spread): Approximately 44.4 cm.

Foliage description:

*General description.*—Leaves basal, simple with approximately 6 per basal rosette, generally symmetrical and long-persisting.

*Leaves.*—Shape: Ovate to slightly carinate. Appearance: Dull. Apex: Apiculate. Base: Obtuse to attenuate. Margin: Entire. Length: Approximately 10.3 cm. Width: Approximately 6.3 cm. Texture of upper and lower surfaces: Smooth, glabrous; furrowed on venation. Venation pattern: Camptodrome. Color of upper surface of young foliage: 139A with a central band of 4C. Color of lower surface of young foliage: 137A to 137B with a central band of 4C. Color of upper surface of mature foliage: Between 137A to 139A with lighter coloration near the base, stripes of 143A to 143B near the edge of and occasionally within the central band of 4C to 5D. Color of lower surface of mature foliage: 137B covered with a glaucous layer of 189A and with a central band of 4C to 4D. Color of upper and lower surfaces of venation: Indistinguishable from leaf color.

*Petiole.*—Length: Approximately 13.7 cm. Diameter: Approximately 6.0 mm. Texture of upper and lower surfaces: Smooth, glabrous. Color of upper surface: 157D with green stripes of 138A to 138B. Color of lower surface: 155A to 157D.

Flowering description:

*Natural flowering season.*—Continuously flowering from June into August in Barneveld, The Netherlands.

*Lastingness of individual flower on the plant.*—Approximately 5 days, not persistent.

Inflorescence description:

*General description.*—Terminal racemes with flowers facing outward or slightly downward. Freely flowering habit with about 22 flowers developing per inflorescence, and approximately 190 individual flowers and buds per plant. Fragrance: None detected. Inflorescence height: Approximately 14.7 cm. Inflorescence diameter: Approximately 8.6 cm.

*Peduncles (scapes).*—Strength: Strong. Length: Approximately 41.5 cm. Diameter: Approximately 3.0 mm. Angle: Erect to approximately a 5° angle from vertical. Texture: Smooth, glabrous. Color: 150D with an occasional longitudinal stripe of 143A.

Flower description:

*Type.*—Campanulate, single.

*Flower buds.*—Rate of opening: Per flowering stem, approximately 5% of the flowers open together with all flowers per inflorescence opening within approximately 4 weeks. Shape: Oblanceolate. Length: Approximately 2.5 cm. Diameter: Approximately 8.0 mm. Color: 76A with spots of 77B, the base is a lighter 69D.

*Perianth.*—Depth: Approximately 4.5 cm. Diameter: Approximately 1.5 cm.

*Tepals.*—Quantity: 6, arranged in a single whorl, fused at base with upper 37% free. Shape: Oblanceolate. Appearance: Dull. Margin: Entire. Apex: Acute. Length: Approximately 3.7 cm. Width: Approximately 9.0 mm. Texture of upper and lower surfaces: Smooth, glabrous. Color of upper (inner) surface when first open: 76A. Color of lower (outer) surface when first open: 76B. Color of upper (inner) surface when fully open: 76A with stripes of 86D. Color of lower (outer) surface when fully open: 76B darkening to 83A with senescence.

*Bracts.*—Quantity: One per flower at the base of the pedicel. Length: Approximately 1.0 cm. Width: Approximately 4.0 mm. Shape: Ovate, concave. Apex: Acute. Base: Cuneate. Margin: Entire. Texture, upper and lower surfaces: Smooth, glabrous. Color, upper and lower surfaces: 155A, transparent.

*Pedicels.*—Length: Approximately 8.0 mm. Diameter: Approximately 1.0 mm. Angle: Approximately 60° from vertical. Strength: Strong. Texture: Smooth, glabrous. Color: 76B to 76C becoming a darker 76A near the base of the flower.

*Reproductive organs.*—Androceium: Quantity per flower: Typically six; anthers dorsifixed. Filament length: Approximately 4.5 cm, curled. Filament color: N155A. Anther shape: Narrowly oblong. Anther length: Approximately 2.0 mm. Anther color: 202A. Pollen amount: Sparse. Pollen color: 12B. Gynoecium: Pistils: Quantity per flower: One. Pistil length: Approximately 4.8 cm. Stigma shape: Crested. Stigma color: 155C. Style length: Approximately 4.7 cm. Style color: N155A. Ovary color: 155A.

Seed and fruit production: Seed and fruit development have not been observed.

Disease and pest resistance: Plants of the new *Hosta* have not been noted to be resistant to pathogens and pests common to *Hosta*.

Garden performance: Plants of the new *Hosta* have been observed to have good garden performance and tolerate rain, wind and high temperatures of about 35° C. (95° F.). Plants of the new *Hosta* have been observed to be hardy to a least USDA Zone 5.

What is claimed is:

1. A new and distinct cultivar of *Hosta* plant named 'Little Treasure', substantially as herein shown and described.

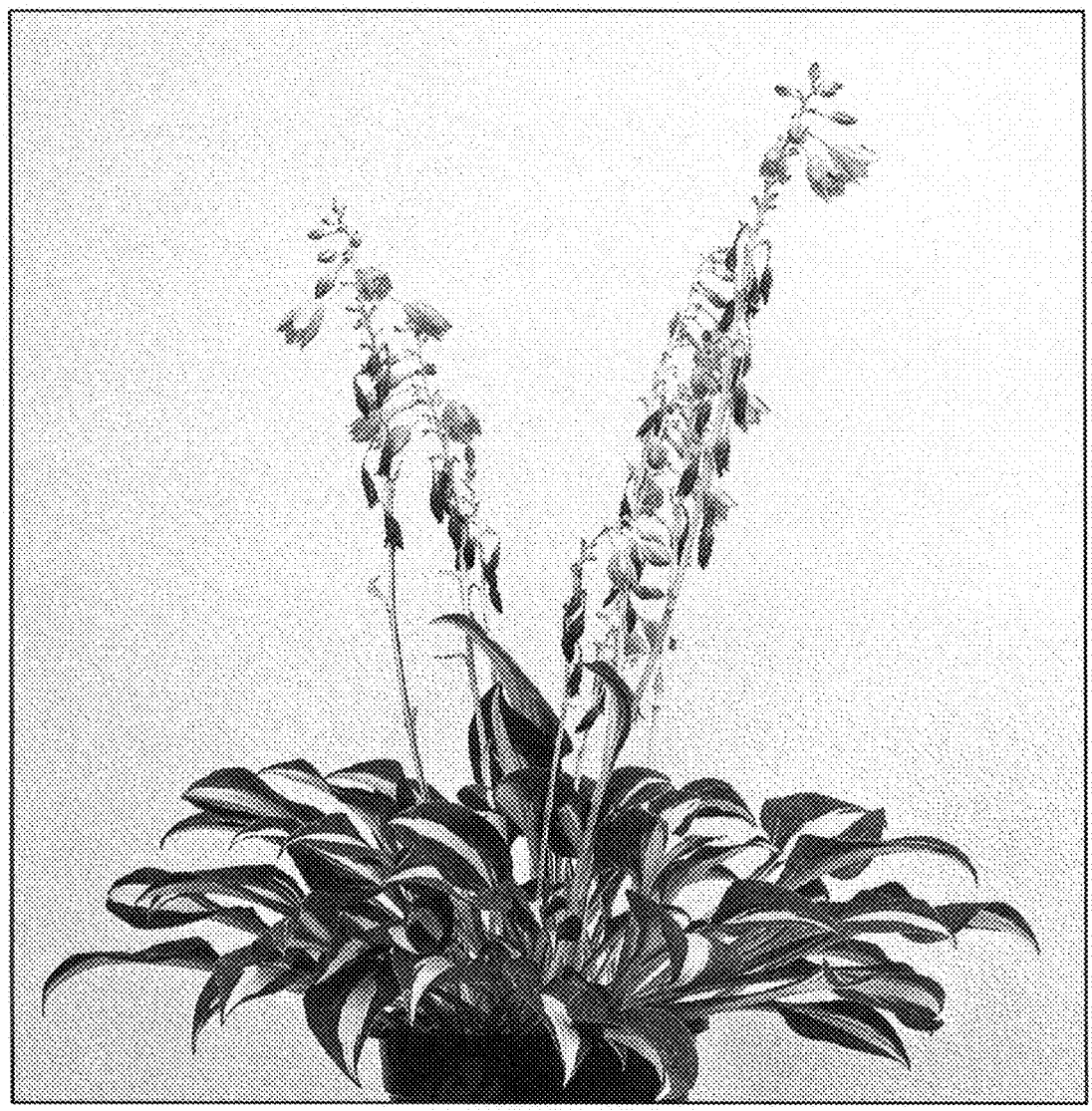

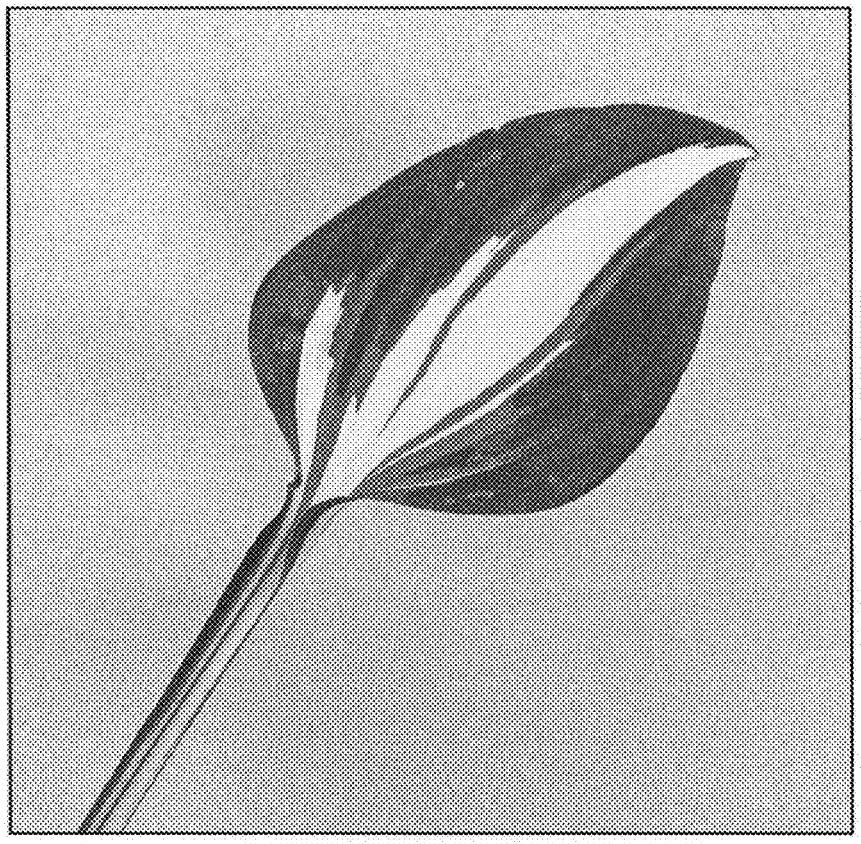
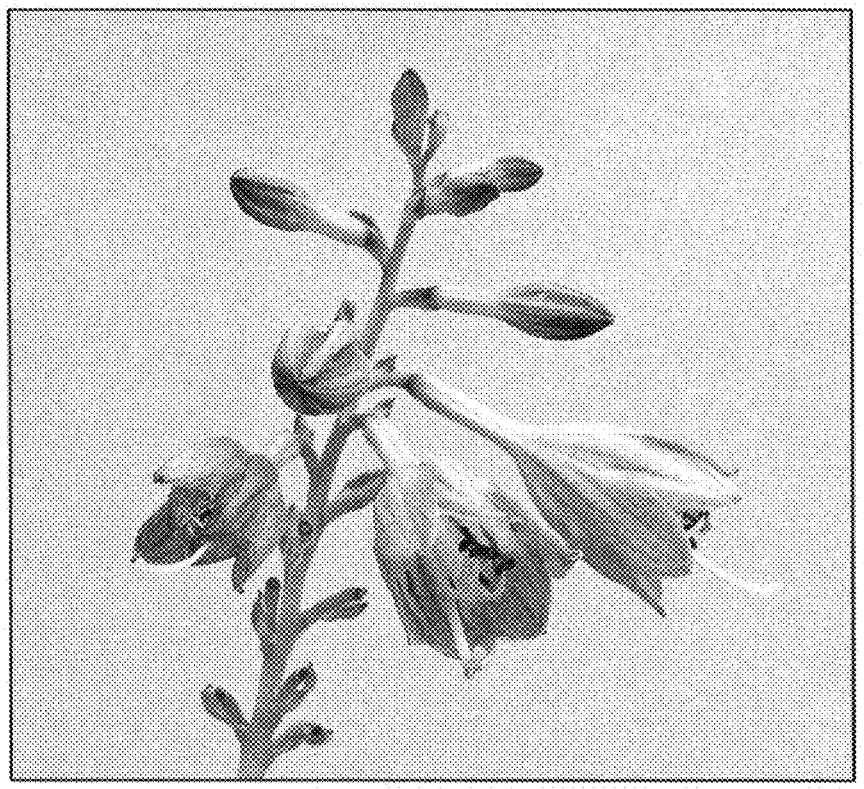

* * * * *